United States Patent [19]

Dharanipragada et al.

[11] Patent Number: 5,734,012
[45] Date of Patent: Mar. 31, 1998

[54] CYCLIC MOTILIN-LIKE POLYPEPTIDES WITH GASTROINTESTINAL MOTOR STIMULATING ACTIVITY

[75] Inventors: Ramalinga Dharanipragada, Sharonville, Ohio; Mark J. Macielag, Branchburg, N.J.; Jung Kim-Dettelback, Dunellen, N.J.; James Florance, Denville, N.J.

[73] Assignee: Ohmeda Pharmaceutical Products Division Inc., Liberty Corner, N.J.

[21] Appl. No.: 648,644

[22] Filed: May 16, 1996

[51] Int. Cl.$^6$ ............... A61K 38/00; C07K 7/00; C07K 7/08; C07K 5/12
[52] U.S. Cl. ............... 530/317; 530/326; 514/9; 514/11; 514/15
[58] Field of Search ............... 514/15, 9, 11; 530/326, 317

[56] References Cited

U.S. PATENT DOCUMENTS

| | | |
|---|---|---|
| 5,084,442 | 1/1992 | Felix et al. ............... 514/10 |
| 5,422,341 | 6/1995 | Macielag et al. ............... 514/13 |

FOREIGN PATENT DOCUMENTS 0 378 078  of 1990  European Pat. Off. .

OTHER PUBLICATIONS

Miller et al., *Peptides*, 16 11–18 (1995)).
Christofides, et al., *Gastroenterology*, 76, 903–907 (1979).
Merrifield, *J. Am. Chem. Soc.* 85, 2149–2154 (1963).
Loffet and Zhang, *Int. J. Peptide Protein Res.* 42, 346–351 (1991).
Felix et al., *Int. J. Peptide Protein Res.*, 31, 231–238 (1988).
Felix et al., *Int. J. Peptide Protein Res.*, 32, 441–454 (1988).
Bouvier et al., *J. Med. Chem.*, 35, 1145–1155 (1992).
Kirby et al., *J. Med. Chem.* 36, 385–393 (1993).
Miranda et al., *J. Med. Chem.*, 37, 1450–1459 (1994).
Kapurniotu et al., *J. Med. Chem.* 38, 836–847 (1995).

*Primary Examiner*—Cecilia J. Tsang
*Assistant Examiner*—S. G. Marshall
*Attorney, Agent, or Firm*—R. Hain Swope; Salvatore P. Pace

[57] ABSTRACT

This invention pertains to cyclic polypeptides having gastrointestinal motor stimulating activity which may be represented by formula (1):

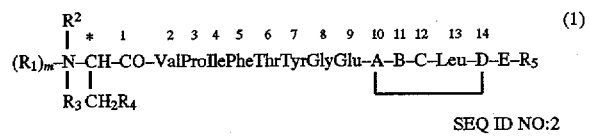

SEQ ID NO:2 including optically active isomeric forms and the pharmaceutically acceptable acid addition salts thereof, wherein groups A and D are linked to from a cyclic structure; and $R_1$ is lower alkyl; $R_2$ is hydrogen or lower alkyl; $R_3$ is hydrogen or lower alkyl; $R_4$ is phenyl or substituted phenyl, wherein the phenyl group may be substituted with one or more substituents selected from the group consisting of halogen, hydroxy, and lower alkoxy; $R_5$ is —OH or —NH$_2$; A is selected from the group consisting of L-glutamic acid, L-aspartic acid, L-lysine, L-ornithine, and L-2,4-diaminobutyric acid; B is L-alanine or L-glutamine; C is L-arginine or D-arginine; D is selected from the group consisting of L-lysine, L-ornithine, L-2,4-diaminobutyric acid, L-glutamic acid, and L-aspartic acid; E is a direct bond between group D and group $R_5$ or is L-lysine or D-lysine; m is 0 or 1; the symbol * represents an asymmetric carbon atom which may be in the D or L configuration, with the proviso that: (a) when A is L-glutamic acid or L-aspartic acid, D is L-lysine, L-ornithine, or L-2,4-diaminobutyric acid; and (b) when A is L-lysine, L-ornithine, or L-2,4-diaminobutyric acid, D is L-glutamic acid or L-aspartic acid. This invention also pertains to methods for using the novel cyclic polypeptides.

18 Claims, No Drawings

CYCLIC MOTILIN-LIKE POLYPEPTIDES WITH GASTROINTESTINAL MOTOR STIMULATING ACTIVITY

FIELD OF THE INVENTION

This invention relates to novel cyclic polypeptides having potent gastrointestinal motor stimulating activity and enhanced metabolic stability. These peptides are useful in the treatment of conditions characterized by a decreased basal level of gastrointestinal motor activity such as diabetic gastroparesis, paralytic ileus, and postoperative ileus. This invention also pertains to methods for using the novel cyclic polypeptides.

BACKGROUND OF THE INVENTION

Motilin is a linear polypeptide hormone that is periodically released from the duodenal mucosa in man and a variety of other species during fasting. Human motilin has only recently been isolated and purified from carcinoid tumor cells [De Clercq et al., *Regulatory Peptides* 55, 79–84 (1995)]. Alternate forms of the peptide which bear considerable sequence homology to human motilin have also been isolated from porcine, canine, feline, and rabbit gastrointestinal tissue. Human motilin contains amino acid residues and may be represented by the formula:

```
      5              10                 15                 20    22
H—Phe—Val—Pro—Ile—Phe—Thr—Tyr—Gly—Glu—Leu—Gln—Arg—Met—Gln—Glu—Lys—Glu—Arg—Asn—Lys—Gly—Gln—OH
```
(SEQ ID NO:1)

Although its physiological role has not been completely defined, it is clear that motilin plays a role in increasing gastric motility and regulating the occurrence of the interdigestive migrating myoelectric complex.

In vitro, motilin induces contractions of isolated human and rabbit duodenal segments. Current evidence suggests that motilin stimulates smooth muscle cell contractility by binding to discrete receptors in the plasma membrane which leads to an increase in calcium influx. In this regard, motilin and some of its derivatives compete with radiolabelled motilin for binding sites on human and rabbit antral tissue.

In vivo, motilin accelerates intestinal transit time and enhances gastric emptying when administered to healthy human subjects. In addition, infusion of motilin has been reported to stimulate the emptying of solids and liquids in patients with diabetic gastroparesis [Peeters et al., *Gastroenterology* 102, 97–101 (1992)]. Moreover, motilin has been used to treat patients with paralytic ileus caused by carcinoma of the gastrointestinal tract [Meyer et al., *Med. Klin.* 86, 515–517 (1991)].

The N-terminal amino acid sequence and certain residues of the midportion of motilin are essential for contractile activity in vitro [Macielag et al., *Peptides* 13, 565–569 (1992); Peeters et al., *Peptides* 13, 1103–1107 (1992); Poitras et al., *Biochem. Biophys. Res. Commun.* 183, 36–40 (1992)]. However, shortened analogs of motilin have little or no activity when administered intravenously, presumably due to rapid metabolic degradation in plasma and the tissues [Raymond et al., *Regul. Pept.* 50, 121–126 (1994)]. Motilin-like polypeptides which have a shorter C-terminus, contain from 3 to 5 basic amino acids bonded from position 12, and have various amino acid substitutions at positions 1 through 11 have been reported to have activity less than, or equal to, that of motilin. None of the motilin-like polypeptides were reported to have increased metabolic stability [Japanese patent no. 2-311,495]. Recently, an extensive series of point-substituted analogs and fragments of motilin was assayed in vitro for contractile effects on rabbit duodenal smooth muscle strips [Miller et al., *Peptides*, 16, 11–18 (1995)]. The potency of these peptides was less than or equal to that of motilin.

A major problem with motilin is its relatively short half-life ($t_{1/2}$) of 4.5 minutes in humans [Christofides et al., *Gastroenterology* 76, 903–907 (1979)]. This short half-life makes it necessary to administer the hormone by continuous infusion to induce a therapeutic effect.

Linear peptides, like motilin, are extremely flexible molecules and exist in multiple conformations in biological media. As a result, each of the peptide bonds in the sequence is exposed to the surrounding milieu and is susceptible to degradation by metabolizing proteases. To date, most of the synthetic analogs of motilin are of the linear configuration. A series of cyclic motilin fragments were reported to be completely devoid of contractile activity in vitro [Miller et al., *Peptides*, 16, 11–18 (1995)]. These peptides were prepared by forming disulfide linkages between strategically placed cysteine residues within the amino terminus of motilin (1–12) amide.

Accordingly, a motilin-like polypeptide having potent gastrointestinal motor stimulating activity and enhanced metabolic stability would be useful for the treatment of decreased basal levels of gastrointestinal motor activity.

SUMMARY OF THE INVENTION

This invention pertains to cyclic polypeptides having gastrointestinal motor stimulating activity which may be represented by formula (1):

$$
\begin{array}{l}
\phantom{(R_1)_m-N-}R^2 \quad\ \ *\ \ 1\ \ 2\ 3\ 4\ 5\ 6\ 7\ 8\ 9\ 10\ 11\ 12\ 13\ 14 \\
(R_1)_m\text{--}N\text{--}CH\text{--}CO\text{--}ValProIlePheThrTyrGlyGlu\text{--}A\text{--}B\text{--}C\text{--}Leu\text{--}D\text{--}E\text{--}R_5 \\
\phantom{(R_1)_m-N-}R_3\ CH_2R_4 \phantom{xxxxxxxxxxxxxxxxxxx}\underline{\phantom{xxxxxxxxxxxx}}
\end{array}
\tag{1}
$$

SEQ ID NO:2 including optically active isomeric forms and the pharmaceutically acceptable acid addition salts thereof, wherein groups A and D are linked to from a cyclic structure; and $R_1$ is lower alkyl;

$R_2$ is hydrogen or lower alkyl;

$R_3$ is hydrogen or lower alkyl;

$R_4$ is phenyl or substituted phenyl, wherein the phenyl group may be substituted with one or more substituents selected from the group consisting of halogen, hydroxy, and lower alkoxy;

$R_5$ is —OH or —NH$_2$;

A is selected from the group consisting of L-glutamic acid, L-aspartic acid, L-lysine, L-ornithine, and L-2,4-diaminobutyric acid;

B is L-alanine or L-glutamine;

C is L-arginine or D-arginine;

D is selected from the group consisting of L-lysine, L-ornithine, L-2,4-diaminobutyric acid, L-glutamic acid, and L-aspartic acid;

E is a direct bond between group D and group $R_5$ or is L-lysine or D-lysine;

m is 0 or 1;

the symbol * represents an asymmetric carbon atom which may be in the D or L configuration, with the proviso that:

(a) when A is L-glutamic acid or L-aspartic acid, D is L-lysine, L-ornithine, or L-2,4-diaminobutyric acid; and (b) when A is L-lysine, L-ornithine, or L-2,4-diaminobutyric acid, D is L-glutamic acid or L-aspartic acid. This invention also pertains to methods for using the novel cyclic polypeptides.

The term

as used herein, means that the tenth amino acid "A" in the peptide chain is attached to the fourteenth amino acid "D" in the chain to form a cyclic (lactam) structure.

The term "cyclo$^{10,14}$", as used herein, means that the peptide is cyclized at the 10 and 14 positions, as defined above.

The term "pMOT", as used herein, refers to porcine or human motilin. Porcine motilin is a polypeptide having the amino acid sequence.

H—Phe—Val—Pro—Ile—Phe—Thr—Tyr—Gly—Glu—Leu—Gln—Arg—Met—Gln—Glu—Lys—Glu—Arg—Asn—Lys—Gly—Gln—OH

SEQ ID NO:3

DETAILED DESCRIPTION OF THE INVENTION

The novel cyclic polypeptides of the present invention bind with high affinity to the motilin receptor and mimic the peristaltic effects of motilin on gastrointestinal tissue. The novel polypeptides also are more effective prokinetic agents in vivo because they demonstrate increased stability to biodegradation in relevant tissue homogenates. The motilin-like polypeptides contain a leucine residue in place of methionine at position 13 for greater chemical stability, a lactam bridge between the side-chains of amino acid residues in positions 10 and 14 to form an eighteen to twenty-one atom membered ring for greater potency and metabolic stability, and an alkylated phenylalanine residue in position 1 for increased stability to biodegradation. The polypeptides of the present invention are therefore useful in the treatment of conditions characterized by a decreased basal level of gastrointestinal motor activity such as diabetic gastroparesis, paralytic ileus, and postoperative ileus.

Cyclization of the peptides of the present invention through intramolecular covalent bond formation enhances metabolic stability by shielding amino acid residues from interaction with proteolytic enzymes. Moreover, the cyclic peptides exhibit greater affinity for their receptor than the corresponding linear analog by existing in a rigid, well-defined molecular shape. Most brain-gut peptides, like motilin, regulate several physiological processes by interacting with receptor subtypes in both the CNS and periphery. Cyclization of the peptide may give it greater specificity for the target receptor and thereby limit undesirable side effects in vivo. The strategy in the present invention for restricting the conformational mobility of the peptide involves the covalent attachment of the basic side-chain of lysine or ornithine with the acidic side-chain of glutamic acid or aspartic acid to form a lactam bridge. In contrast to the hydrophobic nature of cysteine bridges used in the prior art, the amide bond of the lactam possesses considerable dipolar character and can form hydrogen bonds with functional groups of the receptor protein.

The terms "cyclic peptide" or "lactam", as used herein, mean a peptide wherein the side-chain carboxyl group of an acidic amino acid (e.g., Asp or Glu) is attached to the side-chain amino group of a basic amino acid (e.g., Lys or Orn) via the generation of an amide bond (lactam).

The term "pMOT(1–14)", as used herein, means a fragment of porcine motilin having the first fourteen amino acids of the full sequence. In general, numbers in parenthesis following the term "pMOT" indicate fragments of the full pMOT polypeptide.

The following abbreviations employed throughout this specification are defined as set forth below:

| | |
|---|---|
| Phe | phenylalanine |
| Tyr | tyrosine |
| Leu | leucine |
| Ile | isoleucine |
| Val | valine |
| Ala | alanine |
| Gly | glycine |
| Glu | glutamic acid |
| Asp | aspartic acid |
| Lys | lysine |
| Orn | ornithine |
| Dab | 2,4-diaminobutyric acid |
| Arg | arginine |
| Gln | glutamine |
| Asn | asparagine |
| Thr | threonine |
| Pro | proline |
| Me | methyl |
| Alloc | allyloxycarbonyl |
| Boc | t-butyloxycarbonyl |
| 2-Br-Z | 2-bromobenzyloxycarbonyl |
| Bzl | benzyl |
| Cbz | carbobenzyloxy |
| 2-Cl-Z | 2-chlorobenzyloxycarbonyl |
| Dhbt | 3,4-dihydro-4-oxobenzotriazin-3-yl |
| Fmoc | fluorenylmethyloxycarbonyl |
| Mbh | 4,4'-dimethoxybenzhydryl |
| Mtr | 4-methoxy-2,3,6-trimethylbenzenesulfonyl |
| Pfp | pentafluorophenyl |
| Trt | trityl |
| BOP | benzotriazolyloxy-trisdimethylaminophosphonium hexafluorophosphate |
| BOP-Cl | bis(2-oxo-3-oxazolidinyl)phosphinic chloride |
| DCC | N,N'-dicyclohexylcarbodiimide |
| DIC | N,N'-diisopropylcarbodiimide |
| DIEA | diisopropylethylamine |
| DPPA | diphenylphosphorylazide |
| EDAC | N-ethyl-N'-diethylaminopropylcarbodiimide |
| HATU | 2-(1H-7-azabenzotriazol-1-yl)-1,1,3,3-tetramethyluronium hexafluorophosphate |
| HBTU | 2-(1H-benzotriazol-1-yl)-1,1,3,3-tetramethyluronium hexafluorophosphate |
| HEPES | N-[2-hydroxyethyl]piperazine-N'-[2-ethanesulfonic acid] |
| HMPA | hydroxymethylphenoxyacetoxy |
| HOAt | 7-aza-1-hydroxybenzotriazole |
| HOBt | 1-hydroxybenzotriazole |
| MBHA | 4-methylbenzhydrylamino |
| PAM | hydroxymethylphenylacetamidomethyl |

| | |
|---|---|
| PyBOP | benzotriazolyloxy-tripyrrolidinophosphonium hexafluorophosphate |
| PyBrOP | bromo-tripyrrolidinophosphonium hexafluorophosphate |
| DCM | dichloromethane |
| DMF | N,N-dimethylformamide |
| NMM | N-methylmorpholine |
| NMP | N-methylpyrrolidinone |
| TCA | trichloroacetic acid |
| TEA | triethylamine |
| TFA | trifluoroacetic acid |
| TFMSA | trifluoromethanesulfonic acid |

This invention pertains to novel cyclic polypeptides having potent gastrointestinal motor stimulating activity as well as to methods for treating a condition of decreased basal level of gastrointestinal motor activity in a mammal, preferably a human. The methods comprise administering to the mammal an amount, therapeutically effective to relieve the condition, of a polypeptide represented by the formula (1):

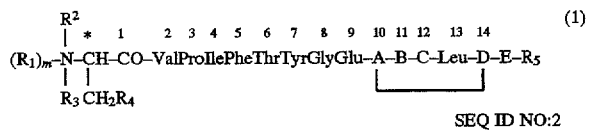

SEQ ID NO:2 including optically active isomeric forms and the pharmaceutically acceptable acid addition salts thereof. In formula (1), m is an integer from 0 to 1, the symbol * represents an asymmetric carbon atom which may be in the D or L configuration, and each lower-alkyl group contains from 1 to 4 carbon atoms, providing that (a) when A is L-glutamic acid or L-aspartic acid, D is L-lysine, L-ornithine, or L-2,4-diaminobutyric acid; and (b) when A is L-lysine, L-ornithine, or L-2,4-diaminobutyric acid, D is L-glutamic acid or L-aspartic acid. Groups A through E and $R_1$ through $R_5$ are defined as set forth below. The novel compounds of the present invention defined by formula (1) are cyclic polypeptides which may be 14 or 15 amino acids in length. The stereochemistry of the constituent amino acids of the novel polypeptides is an essential feature of this invention. The absolute stereochemistry of the individual amino acids is L, unless otherwise noted, except for position 1 (the amino terminal amino acid, $(R_1)_m(R_2)(R_3)N$—*$CH(CH_2R_4)CO$—) which may be L or D, position 12 (Group C) which may be L or D-arginine, and position 15 (when present, Group E) which may be L-lysine or D-lysine.

Position 1, the amino-terminal amino acid, $(R_1)_m(R_2)(R_3)N$—*$CH(CH_2R_4)CO$—

The amino acid in the amino-terminal portion of the polypeptide, $(R_1)_m(R_2)(R_3)N$—*$CH(CH_2R_4)CO$—, in position 1 may have the L or D configuration. $R_1$ is lower-alkyl; $R_2$ and $R_3$ are hydrogen or lower alkyl. The term "lower-alkyl", as used herein, refers to straight- and branched-chain hydrocarbon radicals containing from 1 to 4 carbon atoms. Examples of suitable lower-alkyl groups for $R_1$, $R_2$, and $R_3$ are methyl, ethyl, propyl, isopropyl, butyl, isobutyl, and sec-butyl, preferably methyl.

The integer m is 0 or 1 and preferably is 0. When m is 0, the amino residue may be a primary amine wherein $R_2$ and $R_3$ are hydrogen. The amino residue may also be a secondary amine, tertiary amine, or quaternary ammonium salt (m is 1) substituted by one, two, or three, respectively, lower-alkyl groups having from one to four carbon atoms, and preferably methyl or ethyl. The amino residue may also be substituted by one propargyl group to provide, e.g., N-propargyl, N-methyl-N-propargyl, N,N-dimethyl-N-propargyl substituted amino residues, or up to three allyl groups. Preferably, the amino-terminal amino acid is N-substituted, and the preferred substituents are one to three methyl groups.

$R_4$ is phenyl or substituted phenyl, wherein the phenyl group may be substituted with one or more substituents selected from the group consisting of halogen, hydroxy, and lower alkoxy. Preferred substituted and unsubstituted aryl groups are phenyl, p-fluorophenyl, p-chlorophenyl, p-bromophenyl, p-iodophenyl, p-hydroxyphenyl, and p-methoxyphenyl. For compounds having high levels of gastrointestinal peristaltic activity, the preferred amino-terminal amino acids are L-phenylalanine and D-phenylalanine. Preferred $(R_1)_m(R_2)(R_3)N$—*$CH(CH_2R_4)CO$— groups may be selected from the group consisting of $CH_3NH$—$CH(CH_2C_6H_5)CO$—, $(CH_3)_2N$—$CH(CH_2C_6H_5)CO$—, and $(CH_3)_3N^+$—$CH(CH_2C_6H_5)CO$—.

Position 10, Group A

Group A in position 10 of the polypeptide may be a basic amino acid or an acidic amino acid. When group A is a basic amino acid having an amino side-chain group, it can be linked to the carboxyl side-chain group of the acidic amino acid at group D via the generation of an amide bond to form a lactam. Alternatively, when group A in position 10 of the polypeptide is an acidic amino acid having a carboxyl side chain, it can be linked to the amino side chain group of the basic amino acid at group D via the generation of an amide bond to form a lactam. Examples of basic amino acids may be selected from the group consisting of L-lysine, L-ornithine, and L-2,4-diaminobutyric acid. Examples of acidic amino acids may be selected from the group consisting of L-glutamic acid and L-aspartic acid. The preferred Group A amino acids are L-glutamic acid and L-aspartic acid. When A is L-glutamic acid or L-aspartic acid, group D is L-lysine, L-ornithine, or L-2,4-diaminobutyric acid. When A is L-lysine, L-ornithine, or L-2,4-diaminobutyric acid, group D is L-glutamic acid or L-aspartic acid.

Position 11, Group B

Group B in position 11 of the polypeptide is an amino acid which is L-alanine or L-glutamine. For compounds having high levels of motilin receptor agonist activity, the preferred Group B amino acid is L-alanine.

Position 12, Group C

Group C in position 12 of the polypeptide is an amino acid which is L-arginine or D-arginine. The preferred Group C amino acid is L-arginine.

Position 13, Leu

The motilin-like polypeptides contain a leucine residue in place of methionine at position 13 for greater chemical stability.

Position 14, Group D

Group D in position 14 of the polypeptide may be a basic amino acid or an acidic amino acid. When group D is a basic amino acid having an amino side-chain group, it can be linked to the carboxyl side-chain group of the acidic amino acid group at group A via the generation of an amide bond to form a lactam. Alternatively, when group D in position 14 of the polypeptide is an acidic amino acid having a carboxyl side-chain group, it can be linked to the amino side-chain group of the basic amino acid group at group A via the generation of an amide bond to form a lactam. Examples of basic amino acids may be selected from the group consisting of L-lysine, L-ornithine, and L-2,4-diaminobutyric acid. Examples of acidic amino acids may be selected from the group consisting of L-glutamic acid and L-aspartic acid. The preferred Group D amino acids are L-lysine and L-ornithine, preferably L-lysine.

Group E

Group E in the polypeptide is a direct bond between group D and group $R_5$ or is L-lysine or D-lysine. The preferred Group E amino acid is L-lysine.

Group $R_5$

Group $R_5$ in the polypeptide is —OH or —$NH_2$. The preferred group $R_5$ is —$NH_2$.

The term "halogen", as used herein, includes all four halogens with chlorine being preferred.

In a preferred embodiment, the compounds of the present invention are selected from the group consisting of:

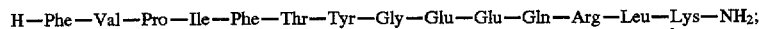

SEQ ID NO:4

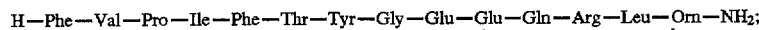

SEQ ID NO:5

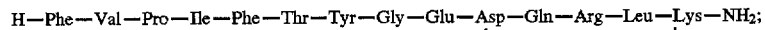

SEQ ID NO:6

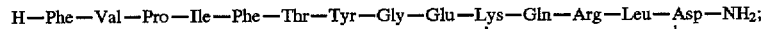

SEQ ID NO:7

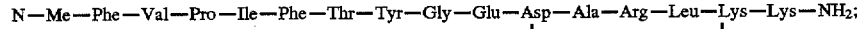

SEQ ID NO:8

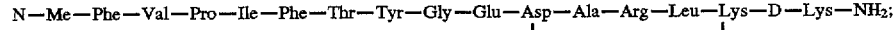

SEQ ID NO:9

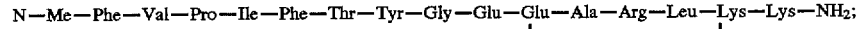

SEQ ID NO:10

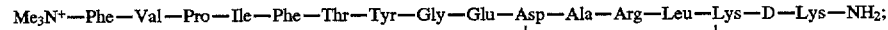

SEQ ID NO:11

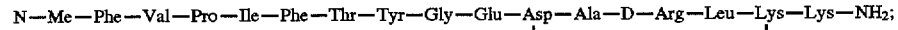

SEQ ID NO:12

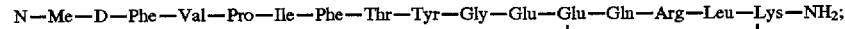

SEQ ID NO:13

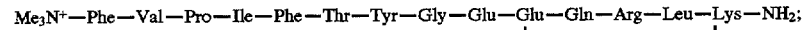

SEQ ID NO:14

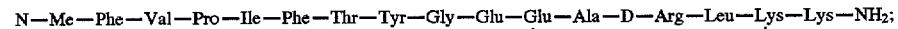

SEQ ID NO:15

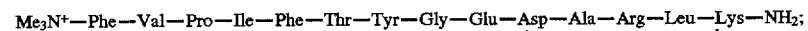

SEQ ID NO:16

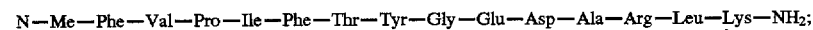

SEQ ID NO:17

SEQ ID NO:18

-continued

SEQ ID NO:19

Me₃N⁺—Phe—Val—Pro—Ile—Phe—Thr—Tyr—Gly—Glu—Glu—Ala—D—Arg—Leu—Lys—Lys—NH₂;

SEQ ID NO:20

Me₃N⁺—Phe—Val—Pro—Ile—Phe—Thr—Tyr—Gly—Glu—Glu—Ala—Arg—Leu—Lys—Lys—NH₂;

SEQ ID NO:21

N—Me—Phe—Val—Pro—Ile—Phe—Thr—Tyr—Gly—Glu—Glu—Gln—Arg—Leu—Lys—NH₂;

SEQ ID NO:22

N—Me—Phe—Val—Pro—Ile—Phe—Thr—Tyr—Gly—Glu—Asp—Ala—D—Arg—Leu—Lys—NH₂;

SEQ ID NO:23

Me₃N⁺—Phe—Val—Pro—Ile—Phe—Thr—Tyr—Gly—Glu—Asp—Ala—D—Arg—Leu—Lys—NH₂;

SEQ ID NO:24 and their pharmaceutically acceptable addition salts. In each case, the amino acids have the L-configuration unless otherwise specified. In a more preferred embodiment, the compounds of the present invention are selected from the group consisting of N—Me—Phe—Val—Pro—Ile—Phe—Thr—Tyr—Gly—Glu—Asp—Ala—Arg—Leu—Lys—Lys—NH₂;

SEQ ID NO:8

N—Me—Phe—Val—Pro—Ile—Phe—Thr—Tyr—Gly—Glu—Asp—Ala—Arg—Leu—Lys—D—Lys—NH₂;

SEQ ID NO:9

N—Me—Phe—Val—Pro—Ile—Phe—Thr—Tyr—Gly—Glu—Glu—Ala—Arg—Leu—Lys—Lys—NH₂;

SEQ ID NO:10

Me₃N⁺—Phe—Val—Pro—Ile—Phe—Thr—Tyr—Gly—Glu—Asp—Ala—Arg—Leu—Lys—D—Lys—NH₂;

SEQ ID NO:11

N—Me—Phe—Val—Pro—Ile—Phe—Thr—Tyr—Gly—Glu—Asp—Ala—D—Arg—Leu—Lys—Lys—NH₂;

SEQ ID NO:12

Me₃N⁺—Phe—Val—Pro—Ile—Phe—Thr—Tyr—Gly—Glu—Glu—Gln—Arg—Leu—Lys—NH₂;

SEQ ID NO:14

N—Me—Phe—Val—Pro—Ile—Phe—Thr—Tyr—Gly—Glu—Glu—Ala—D—Arg—Leu—Lys—Lys—NH₂;

SEQ ID NO:15

Me₃N⁺—Phe—Val—Pro—Ile—Phe—Thr—Tyr—Gly—Glu—Asp—Ala—Arg—Leu—Lys—NH₂;

SEQ ID NO:16

N—Me—Phe—Val—Pro—Ile—Phe—Thr—Tyr—Gly—Glu—Asp—Ala—Arg—Leu—Lys—NH₂;

SEQ ID NO:17

Me₃N⁺—Phe—Val—Pro—Ile—Phe—Thr—Tyr—Gly—Glu—Asp—Ala—Arg—Leu—Lys—Lys—NH₂;

SEQ ID NO:18

Me₃N⁺—Phe—Val—Pro—Ile—Phe—Thr—Tyr—Gly—Glu—Asp—Ala—D—Arg—Leu—Lys—Lys—NH₂;

SEQ ID NO:19

Me₃N⁺—Phe—Val—Pro—Ile—Phe—Thr—Tyr—Gly—Glu—Glu—Ala—D—Arg—Leu—Lys—Lys—NH₂;

SEQ ID NO:20

-continued

Me₃N⁺—Phe—Val—Pro—Ile—Phe—Thr—Tyr—Gly—Glu—Glu—Ala—Arg—Leu—Lys—Lys—NH₂;
                                                            |_____|

SEQ ID NO:21

N—Me—Phe—Val—Pro—Ile—Phe—Thr—Tyr—Gly—Glu—Glu—Gln—Arg—Leu—Lys—NH₂;
                                                        |_____|

SEQ ID NO:22

N—Me—Phe—Val—Pro—Ile—Phe—Thr—Tyr—Gly—Glu—Asp—Ala—D—Arg—Leu—Lys—NH₂;
                                                    |_____|

SEQ ID NO:23 and their pharmaceutically acceptable addition salts. In a most preferred embodiment, the compounds of the present invention are selected from the group consisting of N—Me—Phe—Val—Pro—Ile—Phe—Thr—Tyr—Gly—Glu—Glu—Ala—Arg—Leu—Lys—Lys—NH₂;
                                                        |_____|

SEQ ID NO:10

N—Me—Phe—Val—Pro—Ile—Phe—Thr—Tyr—Gly—Glu—Asp—Ala—Arg—Leu—Lys—NH₂;
                                                    |_____|

SEQ ID NO:17

Me₃N⁺—Phe—Val—Pro—Ile—Phe—Thr—Tyr—Gly—Glu—Glu—Ala—Arg—Leu—Lys—Lys—NH₂;
                                                        |_____|

SEQ ID NO:21

Me₃N⁺—Phe—Val—Pro—Ile—Phe—Thr—Tyr—Gly—Glu—Asp—Ala—Arg—Leu—Lys—D—Lys—NH₂;
                                                        |_____|

SEQ ID NO:11

Me₃N⁺—Phe—Val—Pro—Ile—Phe—Thr—Tyr—Gly—Glu—Asp—Ala—Arg—Leu—Lys—Lys—NH₂;
                                                        |_____|

SEQ ID NO:18

N—Me—Phe—Val—Pro—Ile—Phe—Thr—Tyr—Gly—Glu—Glu—Gln—Arg—Leu—Lys—NH₂;
                                                        |_____|

SEQ ID NO:22 and their pharmaceutically acceptable addition salts.

The compounds of the present invention can be prepared by various methods known in the art such as by solid phase peptide synthesis or by classical solution phase synthesis. The peptides are preferably prepared by the solid phase method as described by Merrifield, *J. Am. Chem. Soc.* 85, 2149–2154 (1963). The synthesis is carried out by constructing the peptide on a resin support, typically a polystyrene based, polyhipe based, polystyrene-polyethylene glycol graft copolymer, or a polyacrylamide/Kieselguhr composite resin. The growing peptide chain is tethered to the solid support by a suitable, molecular linker, such as hydroxymethylphenoxyacetoxy (HMPA), hydroxymethylphenylacetamidomethyl (PAM), or 4-methylbenzhydrylamino (MBHA). The peptide chain can then be cleaved from the linker, and thus the resin support through acidolysis employing hydrogen fluoride, trifluoroacetic acid (TFA), trifluoromethanesulfonic acid (TFMSA), and the like.

Whether the gastrointestinal motor stimulating polypeptides of this invention are prepared by solid phase or solution phase methods, the basic synthetic approach for assembling the linear peptide precursor involves coupling of amino acid subunits through reaction of the carboxyl moiety of one suitably protected amino acid or peptide fragment with the amino group of another suitably protected amino acid or peptide fragment to form a new amide bond. In order to effect the coupling reaction, the carboxyl moiety must be activated. Activation is accomplished through the use of standard coupling reagents such as DCC, DIC, EDAC, BOP, HBTU, PyBOP, PyBrOP, or HATU. Except in the case of PyBrOP, an equimolar amount of HOBt or HOAt may be added to suppress racemization of the activated amino acid component. Bases such as NMM, DIEA, or TEA may be used in those cases where it is necessary to employ the carboxylate salt of the corresponding amino acid for activation.

Alternatively, the peptides of this invention can be synthesized by coupling the active esters of the component amino acids. Such active esters include, for example, a pentachlorophenyl ester, a Pfp ester, a p-nitrophenyl ester, a Dhbt ester, and the like.

During the preparation of the peptides of this invention, other reactive functionalities of the amino acid components must be blocked with appropriate protecting groups. In general, the identity of the α-amino blocking group dictates what type of side-chain protecting groups must be employed. For example, in the case where the a-amino group is protected as its Boc derivative, side-chain protection is usually accomplished with ester, ether, urethane, or carbonate derivatives of benzyl alcohol. Ester and ether derivatives of cyclohexanol have also been used with some success. In contrast, when the α-amino group is protected as its Fmoc derivative, side-chain functionality is generally protected as ester, ether or urethane derivatives of t-butanol. Alternatively, the side-chain functionality may be protected as ester or urethane derivatives of allyl alcohol when using either the Boc or Fmoc approach. Of course, alternative combinations of protecting groups may be employed especially when the peptides of this invention are synthesized by solution phase methodology.

Removal of the Fmoc α-amino protecting group can be readily accomplished with a base, typically piperidine or diethylamine. The side-chain protecting groups can be removed by treatment with TFA in the presence of an appropriate carbonium ion scavenger, which also cleaves the bond between the C-terminus of the peptide and the resin linker. The Boc protecting group is typically removed by treatment with dilute TFA. Following TFA cleavage, however, the α-amino group is present as its TFA salt. In order to make the α-amino group of the growing peptide chain reactive toward the next amino acid derivative, the resin-bound peptide is neutralized with a base such as TEA or DIEA. Strong acid, such as hydrofluoric acid or TFMSA, containing suitable scavengers is then used to deprotect the amino acid side-chains and to cleave the peptide from the resin support. With either the Fmoc or Boc strategies, selective deprotection of allyloxycarbonyl or allyl ester functionalities can be readily accomplished by treatment with $Pd^0$ in the presence of a suitable nucleophile, such as morpholine, dimedone, or tri-n-butyltin hydride [Loffet and Zhang, *Int. J. Peptide Protein Res.* 42, 346–351 (1993)].

Side-chain to side-chain cyclization on the solid support demands the use of an orthogonal strategy which enables the selective removal of the protecting groups on the side-chains of the residues to be cyclized. The 9-fluorenylmethyl (OFm) protecting group for the side-chains of Asp and Glu and the 9-fluorenylmethoxycarbonyl (Fmoc) protecting group for the side-chain of Lys, Orn, and Dab can be used for this purpose. In these cases, the side-chain protecting groups (OFm and Fmoc) of the Boc-protected peptide-resin are selectively removed with piperidine in DMF. Alternatively, the allyl and the allyloxycarbonyl (Alloc) protecting groups can be used for the side-chains of Asp/Glu and Lys/Orn/Dab, respectively. In these cases the side-chain protecting groups (allyl and Alloc) of the Boc- or Fmoc-protected peptide-resin are selectively removed with $Pd^0$ in the presence of a suitable nucleophile, like tri-n-butyltin hydride or dimedone. Cyclization is achieved on the solid support using various activating agents including DCC, DCC/HOBt, BOP, PyBOP, BOP-Cl, or DPPA. Cyclization may be effected at any point in the synthesis, once the residues to be cyclized have been incorporated into the growing peptide chain. In the case of the peptides of the present invention, cyclization is preferentially accomplished following assembly of the full-length linear precursor peptide. Deprotection and cleavage of the peptide from the solid support is then effected under acidolytic conditions as described above.

In accord with the present invention, a process is provided for the preparation of peptides which contain the amino terminal portion, $(R_1)_m(R_2)(R_3)N-$. When m=1 and $R_2$ and $R_3$ are lower-alkyl, the method comprises reacting the N-terminal amino group $(NR_2R_3-(AA)_n-)$ of a suitably protected peptide, optionally bound to an insoluble support through an appropriate linker, with a compound represented by the formula $R_1Hal$, wherein $R_1$ is defined above and Hal is a halogen atom. The reaction is carried out in a suitable solvent, such as DMF or NMP, in the presence of a suitable acid-binding agent, such as sodium carbonate or potassium carbonate. The method is more fully described in Benoiton-Chen, *Proced. 14th Europ. Pept. Symp.*, (1976), p.149, which disclosure is incorporated herein by reference. Such alkylation of the N-terminal amino group with an alkyl halide in the presence of an acid-binding agent may be effected either before or after formation of the cyclic peptide backbone. In the case of the peptides of the present invention, alkylation is preferentially accomplished following side-chain to side-chain cyclization.

The compounds of the present invention while effective in the form of the free base may be formulated and administered in the form of pharmaceutically acceptable acid addition salts for purposes of stability, convenience of crystallization, increased solubility and the like. These acid addition salts are formed by conventional methods from suitable inorganic or organic acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, methanesulfonic, naphthalenesulfonic, propionic acid, and the like. Preferably, the acid addition salts are those prepared from hydrochloric acid, acetic acid, or succinic acid.

The compounds of the present invention can be combined with a pharmaceutically acceptable carrier to provide a pharmaceutical composition. Suitable carriers for the subject compounds as the free base include propylene glycol-alcohol-water, isotonic water, sterile water for injection (USP), emulPhor TM-alcohol-water, cremophor-EL TM or other suitable carriers known to those skilled in the art.

Suitable carriers for the acid addition salts of the subject compounds include isotonic water, sterile water for injection (USP), alone or in combination with other solubilizing agents such as ethanol, propylene glycol, or other conventional solubilizing agents known to those skilled in the art. A preferred carrier is an isotonic aqueous solution of the inventive compound.

The compounds of the present invention can be administered to mammals, e.g., animals or humans, in amounts effective to provide the desired gastrointestinal motor stimulating activity. Since the activity of the compounds and the degree of the desired therapeutic effect vary, the dosage level of the compound employed will also vary. The actual dosage administered will also be determined by such generally recognized factors as the body weight of the patient and the individual hypersensitiveness of the particular patient. Thus, the unit doasge for a particular patient (man) can vary from as low as about 0.1 µg per kg of body weight, which the practitioner may titrate to the desired effect. A preferred minimum dose for titration is 1 µg/kg body weight.

The compounds of the present invention can be administered by recognized parenteral routes, in the form of sterile solutions or suspensions, in the carriers previously described. These preparations should contain at least about 0.1%, by weight, of the inventive compound but this amont may be varied to between about 0.1% and about 50%, by weight, of the inventive compound. The compounds of the present invention are preferably administered intravenously and the dosage used will generally be in the range from about 0.1 µg to about 500 mg, and preferably from about 1 µg to about 50 mg, per 70 kg body weight. This dosage may be adminstered from 1 to 4 times daily.

The sterile solutions or suspensions may also include the following adjuvants: a sterile diluent, such as water for injection, saline solution, fixed oils, polyethylene glycol, glycerine, propylene glycol, or other synthetic solvent; antibacterial agents, such as benzyl alcohol or methyl paraben; antioxidants, such as ascorbic acid or sodium metabulsulfite; chelating agents, such as ethylenediaminetetraacetic acid (EDTA); buffers, such as acetates, citrates or phosphates; and agents for the adjustment of tonicity, such as sodium chloride or dextrose. The parenteral preparations may be enclosed in ampules, disposable syringes, or multiple dosage vials made of glass or plastic.

Throughout this application, various publications have been referenced. The disclosures in these publications are incorporated herein by reference in order to more fully describe the state of the art.

The present invention is further illustrated by the following examples which are presented for purposes of demonstrating, but not limiting, the preparation of the compounds and compositions of this invention.

Example 1

Synthesis of Cyclo$^{10,14}$[Asp$^{10}$,Leu$^{13}$,Lys$^{14}$]motilin-(1–14)-peptide Amide (Porcine) Bis-Trifluoroacetate Salt The polypeptide was synthesized on 1g of MBHA resin (1% cross-linked divinyl benzene-styrene: 200–400 mesh size; substitution: 0.27 meq/g) by solid phase techniques employing a Milligen Model 9600 peptide synthesizer. All residues were coupled using t-Boc amino acids and DIC as the condensing agent. The side-chain protection was as follows: Arg(Tos), Asp(OFm), Glu(OBzl), Lys (Fmoc), Thr (Bzl), Tyr (2-Br-Z). When coupling Gln, 1.2 eq of HOBt was used to suppress dehydration. Amino acid residues Phe$^1$, Val$^2$, Pro$^3$, Ile$^4$, Phe$^5$ and Lys$^{14}$ were double coupled (2 hours each). The remainder of the amino acid residues were single coupled (2 hours each). A 6.67 molar excess of amino acid was used for each coupling. After coupling of Boc-Phe$^1$, the side-chain OFm and Fmoc protecting groups on Asp$^{10}$ and Lys$^{14}$ respectively were removed by treating the resin for 2 minutes with 50 mL of 20% piperidine in DMF. The resin was washed with DMF (3×25 mL). Another portion (50 mL) of 20% piperidine in DMF was added and the resin mixed for 15 minutes. Once again, the resin was washed with DMF (3×25 mL). The piperidinium salt of the resin-bound peptide was exchanged for the triethylammonium salt by treating the resin with 20% triethylamine in DMF for 15 minutes. The resin was then washed with DMF (3×25 mL). The ninhydrin test was positive for free amines. Side-chain to side-chain cyclization of the amino group of Lys$^{14}$ and the carboxyl group of Asp$^{10}$ was accomplished by suspending the resin in 20 mL of NMP and adding 720 mg (6 eq) of BOP and 250 mL (6 eq) of triethylamine. The mixture was stirred for 10 hours. The reagents were drained and the resin was washed with DMF (3×25 mL). The resin-bound peptide was treated again with 720 mg (6 eq) of BOP and 250 mL (6 eq) of triethylamine (2×10 hours). The resin was washed with DMF (3×25 mL) and DCM (3×25 mL). The ninhydrin test was negative for free amines. The resin was dried under vacuum overnight. The peptide was cleaved from the resin using liquid HF: anisole (10:1) at −10° to 0° C. for 1 hour. Following evaporation of the HF, the peptide was extracted into 15% aqueous acetic acid and lyophilized to give 400 mg (87%) of a light yellow powder. Purification of this crude peptide was accomplished by preparative HPLC with a Waters Delta-Prep 3000 system using three C-18 columns in series (250×20 mm, 15 µ, Vydac). The solvent system was 0.1% TFA: acetonitrile with a 30 minute gradient (20 to 60% acetonitrile) at 20 mL/min with UV detection at 230 nm. The purity of individual fractions was assessed by analytical HPLC (0 to 100% acetonitrile in 30 minutes with 0.1% TFA as the buffer) with UV detection at 214 nm (ret. time=16.3 min). Pure fractions were pooled and lyophilized to provide 86 mg (16%) of the title peptide as a flocculent white powder.

AAA: Asn/Asp 0.88 (1), Thr 0.88 (1), Gln/Glu 2.02 (2), Pro 1.01 (1), Gly 1.01 (1), Val 0.90 (1), Ile 0.93 (1), Leu 1.00 (1), Tyr 0.97 (1), Phe 1.94 (2), Lys 0.89 (1), Arg 1.01 (1). FAB-MS: (M+H)$^+$calcd: 1693.91, found 1694.60.

Example 2

Synthesis of Cyclo$^{10,14}$[N-MethylPhe$^1$,Glu$^{10}$, Ala$^{11}$, Leu$^{13}$, Lys$^{14}$]motilin-(1–14)-peptide Amide (Porcine) Bis-Trifluoroacetate Salt SEQ ID NO:25

The polypeptide was synthesized on 1 g of MBHA resin (1% cross-linked divinyl benzene-styrene: 200–400 mesh size; substitution: 0.27 meq/g) by solid phase techniques employing a Milligen Model 9600 peptide synthesizer. All residues were coupled using t-Boc amino acids and DIC as the condensing agent. The side-chain protection was as follows: Arg(Tos), Glu$^{10}$(OFm), Glu$^9$(OBzl), Lys(Fmoc), Thr(Bzl), Tyr(2-Br-Z). When coupling Gln, 1.2 eq of HOBt was used to suppress dehydration. Amino acid residues N-Me-Phe$^1$, Val$^2$, Pro$^3$, Ile$^4$, Phe$^5$ and Lys$^{14}$ were double coupled (2 hours each). The remainder of the amino acid residues were single coupled (2 hours each). A 6.67 molar excess of amino acid was used for each coupling. Boc-N-Me-Phe was coupled using 4 eq of BOP, 4 eq of DIEA, and 4 eq of HOBt. After coupling Boc-N-Me-Phe$^1$, the side-chain OFm and Fmoc protecting groups on Glu$^{10}$ and Lys$^{14}$ respectively were removed by treating the resin for 2 minutes with 50 mL of 20% piperidine in DMF. The resin was washed with DMF (3×25 mL). Another portion (50 mL) of 20% piperidine in DMF was added and the resin mixed for 15 minutes. Once again, the resin was washed with DMF (3×25 mL). The piperidinium salt of the resin-bound peptide was exchanged for the triethylammonium salt by treating the resin with 20% triethylamine in DMF for 15 minutes. The resin was then washed with DMF (3×25 mL). The ninhydrin test was positive for free amines. Side-chain to side-chain cyclization of the amino group of Lys$^{14}$ and carboxyl group of Glu$^{10}$ was accomplished by suspending the resin in 20 mL of NMP and adding 720 mg (6 eq) of BOP and 250 mL (6 eq) of triethylamine. The mixture was stirred for 10 hours. The reagents were drained and the resin was washed with DMF (3×25 mL). The resin-bound peptide was treated again with 720 mg (6 eq) of BOP and 250 mL (6 eq) of triethylamine cyclization was repeated (2×10 hours). The resin was washed with DMF (3×25 mL) and DCM (3×25 mL). The ninhydrin test was negative for free amines. The resin was dried under vacuum overnight. The peptide was cleaved from the resin using liquid HF: anisole (10:1) at −10° to 0° C. for 1 hour. Following evaporation of the HF, the peptide was extracted into 15% aqueous acetic acid and lyophilized to give 200 mg (45%) of a light yellow powder. Purification of this crude peptide was accomplished by preparative HPLC with a Waters Delta-Prep 3000 using three C-18 columns in series (250×20 mm, 15 µ, Vydac). The solvent system was 0.1% TFA: acetonitrile with a 30 minute gradient (20 to 60% acetonitrile) at 20 mL/min with UV detection at 230 nm. The purity of individual fractions was assessed by analytical HPLC (0 to 100% acetonitrile in 30 minutes with 0.1% TFA as the buffer) with UV detection at 214 nm (ret. time=18.2 min). Pure fractions were pooled and lyophilized to provide 40 mg (10%) of the title peptide as a flocculent white powder.

AAA: Thr 1.00 (1), Gln/Glu 1.10 (1), Pro 1.10 (1), Gly 1.10 (1), Ala 1.10 (1), Val 0.87 (1), Ile 1.00 (1), Leu 2.20 (2), Tyr 1.10 (1), Phe 1.10 (1), Lys 2.20 (2), FAB-MS: (M+H)$^+$calcd: 1621.0, found: 1621.0.

Example 3

Synthesis of Cyclo$^{10,14}$[N,N,N-TrimethylPhe$^1$, Glu$^{10}$, Ala$^{11}$,Leu$^{13}$, Lys$^{14}$]motilin-(1–14)-peptide Amide(Porcine) Bis-Trifluoroacetate Salt SEQ ID NO:26

The polypeptide was synthesized on 1 g of MBHA resin (1% cross-linked divinyl benzene-styrene: 200–400 mesh size; substitution: 0.27 meq/g) by solid phase techniques employing a Milligen Model 9600 peptide synthesizer. All residues were coupled using t-Boc amino acids and DIC as the condensing agent. The side-chain protection was as follows: Arg(Tos), Glu$^{10}$(OFm), Glu$^9$(OBzl), Lys(Fmoc), Thr(Bzl), Tyr(2-Br-Z). When coupling Gln, 1.2 eq of HOBt was used to suppress dehydration. Amino acid residues Phe$^1$ Val$^2$, Pro$^3$, Ile$^4$, Phe$^5$ and Lys$^{14}$ were double coupled (2 hours each). The rest of the amino acid residues were single coupled (2 hours each). A 6.67 molar excess of amino acid was used for each coupling. After coupling Boc-Phe$^1$, the side-chain OFm and Fmoc protecting groups on Glu$^{10}$ and Lys$^{14}$ respectively were removed by treating the resin for 2 minutes with 50 mL of 20% piperidine in DMF. The resin was washed with DMF (3×25 mL). Another portion (50 mL) of 20% piperidine in DMF was added and the resin mixed for 15 minutes. Once again, the resin was washed with DMF (3×25 mL). The piperidinium salt of the resin-bound peptide was exchanged for the triethylammonium salt by treating the resin with 20% triethylamine in DMF for 15 minutes. The resin was then washed with DMF (3×25 mL). The ninhydrin test was positive for free amines. Side-chain to side-chain cyclization of the amino group of Lys$^{14}$ and carboxy group of Glu$^{10}$ was accomplished by suspending the resin in 20 mL of NMP and adding 720 mg (6 eq) of BOP and 250 mL (6 eq) of triethylamine. The mixture was stirred for 10 hours. The reagents were drained and the resin was washed with DMF (3×25 mL). The resin-bound peptide was treated again with 720 mg (6 eq) of BOP and 250 mL (6 eq) of triethylamine (2×10 hours). The resin was washed with DMF (3×25 mL) and DCM (3×25 mL). The ninhydrin test was negative for free amines. The t-Boc group on Phe$^1$ was removed by treating the resin with 50 mL of 50% TFA in DCM containing anisole (5%) as a scavenger (1×2 min followed by 1×15 min). The resin was washed with DCM (2×50 mL), 20% DIEA in DCM (2×50 mL), 20% DIEA in DMF (1×50 mL), and finally DMF (3×50 mL). The resin was suspended in 20 mL of DMF. To this suspension, 5 mL of methyl iodide and 0.5 g of sodium carbonate were added and the mixture stirred for 20 h. The resin was filtered and washed with DMF (5×50 mL) and DCM (5×50 mL) and dried under vacuum overnight. The peptide was cleaved from the resin using liquid HF: anisole (10:1) at −10° to 0° C. for 1 hour. The peptide was extracted into 15% aqueous acetic acid and lyophilized to give 400 mg (87%) of a light yellow powder. Purification of this crude peptide was accomplished by preparative HPLC with a Waters Delta-Prep 3000 using three C-18 columns in series (250×20 mm, 15 µ, Vydac). The solvent system was 0.1% TFA: acetonitrile with a 30 minute gradient (20 to 60% acetonitrile) at 20 mL/min with UV detection at 230 nm. The purity of individual fractions was assessed by analytical HPLC (0 to 100% acetonitrile in 30 minutes with 0.1% aq TFA as the buffer A) with UV detection at 214 nm; Ret. time=17.6 min). Pure fractions were pooled and lyophilized to provide 56 mgs (12%) of the title peptide as a flocculent white powder. AAA: Thr 0.96 (1), Gln/Glu 2.10 (2), Pro 1.03 (1), Gly 1.08 (1), Val 0.11 (1), Ile 1.00 (1), Leu 2.15 (2), Tyr 1.03 (1), Phe 1.06 (1), Lys 2.06 (2). FAB-MS: (M+H)$^+$calcd: 1706.0, found 1705.8.

Example 4

In vitro stability testing in 2% hog kidney homogenate

Like most small linear polypeptides, motilin is believed to be metabolized by the brush border cells of the kidney. Therefore, kidney homogenate was chosen as the model system for assessing the relative in vivo biostability of the peptides of this invention. All peptides to be studied were incubated in hog kidney (Pel Freeze, Inc., Rogers, Ark.) (2% w/v; final volume=4 mls; buffer=HEPES pH 7.0) at 25° C. Both initial substrate concentration and internal standard (Fmoc-Gly) concentration were 0.5 mg/ml. In order to determine suitable incubation times and sampling intervals, two experiments were conducted with each polypeptide. The first run served as a rough estimate of peptide stability. All sampling was performed in duplicate. Sample volume was 180 µl.

Sample clean-up was performed by addition of 20 µl of 100% TCA (final volume=200 µl; final TCA concentration=10%). The sample was vortexed from 5 to 10 seconds to ensure equilibration, then centrifuged to spin out the precipitated proteins. Analysis was carried out on a Waters HPLC system with autoinjector, a 5 µVydac C-18 analytical column, and a Waters 481 UV detector set at 214 nm. Injection volume was 80 µl. Initial solvent conditions were 20% acetonitrile / 80% (0.1%) TFA in Milli-Q water with a 35 minute gradient running to 63% acetonitrile / 37% (0.1%) TFA at 1 ml/min.

Polypeptide substrate and metabolite peaks were ratioed to the internal standard and the duplicate sample ratios were averaged. The average ratio for the peptide substrate was expressed as a percentage and plotted versus time. First-order kinetics was assumed for data treatment. The rate of disappearance of the substrate was calculated using the Enzfitter program (Biosoft). Relative half-lives were determined from the relationship:

$$t_{1/2}=0.693/k.$$

Example 5

Determination of motilin receptor binding affinity

The motilin receptor binding affinity of the peptides of this invention was determined by using the general procedure of Bormans, Peeters and Vantrappen, *Regul. Pept.*, 15, 143–153 (1986). The ability of the peptides to displace [125I-Tyr7,Nle13]motilin(porcine) bound to rabbit antral smooth muscle membranes, was determined by testing twice, each time in duplicate, at concentrations ranging from $10^{-11}$ to $10^{-4}$ M. The concentration displacing 50% of the label (IC$_{50}$) was determined by fitting the data to the equation describing displacement, assuming a single class of motilin receptors to which labeled and non-labeled motilin bind with equal affinity and non-cooperatively. Fitting was performed using the iterative least-squares procedure of the SAS-software package (SAS Institute, Inc., Cary, N.C., USA). From a large series of control experiments the dissociation constant of motilin itself was calculated as 0.75 nM (pK$_d$=9.12), and this value was used for all calculations. The concentration displacing 50% of the label is expressed using its negative logarithm (pIC$_{50}$).

Example 6

Rabbit duodenal smooth muscle strip tissue bath assay

The contractile response of segments of rabbit duodenum was determined isotonically in the tissue bath according to the procedure of Depoortere et al., *J. Gastrointestinal Motility*, 1, 150–159 (1989). The experimental protocol consisted of an equilibration period of 1 hour; a challenge with $10^{-4}$ M acetylcholine followed by a wash-out period; a cumulative dose-response curve of a compound with, at the end, the addition of $10^{-7}$ M motilin; and finally $10^{-4}$ M acetylcholine. If the final response to $10^{-4}$ M acetylcholine differed by more than 5% from the initial response, the results were discarded. The compounds were tested in the concentration range $10^{-11}$ to $10^{-4}$ M. The point corresponding to 50% of the maximal response to motilin ($E_{max}$) was determined by fitting the equation $E=E_{max} (1+EC_{50}/[L])$ through the data points. For weakly active compounds 90% of the response to $10^{-7}$ M motilin was used as Emax. The dose giving 50% of the response is expressed using its negative logarithm ($pEC_{50}$).

Example 7

Contractile activity in the canine gastrointestinal tract

Mongrel dogs of either sex were anesthetized with sodium pentobarbital 65 mg/kg intravenously. A mid-line incision was made in the abdomen. A duodenal segment was located, the terminal arteries to that segment were identified, and the closest possible artery of the appropriate size was rubbed clean of fat and fascia. A needle of suitable diameter was bent at an angle and the tip inserted in the cleaned artery. The needle was held in position in the artery for approximately 30 seconds until vascular spasm had relaxed and then a catheter assembly was inserted into the artery and tied into position with 000 silk sutures. The fine polyethylene catheter (10–15 cm) was cut to a point at one end with a needle inserted at the other end. The hub of the needle was fitted with a 3-way stopcock and the catheter assembly was filled with heparinized Krebs Ringer bicarbonate containing 10 mM glucose. A bolus of Krebs (free of air) was injected into the arterial catheter and the distribution of blanching in the segment noted. If the area was too large, collateral arteries were tied off as long as circulation to the area was maintained. A Bass type strain gauge was then sutured to the serosa, oriented so that circular muscle contractions could be recorded on a Beckman R611 dynograph. Silver wire electrodes were inserted subserosally on either side of the strain gauge and were connected through stimulus isolation units to a Grass S88 electrical stimulator. Electrical field stimulation was applied at 40V 0.5 ms and 5 pps and the amplitude of the pen recorder was set to contain the contractile response.

All peptides to be injected were dissolved in Krebs and serial dilutions were prepared so that for any concentration the maximum volume to be injected is 1 ml. All solutions except stock Krebs were held on ice for the day of the experiment and discarded at the end of the day. For determination of a dose-response curve, the site was first injected with a bolus of approximately 1 ml of heparinized Krebs to provide a flush control. Peptide agonists (in volumes of 1 ml) were injected in logarithmic increments until a response which is maximal in amplitude was obtained. The injection site was then flushed with Krebs containing 0.1% BSA to displace any peptide remaining in the arterial line. For peptides acting at the motilin receptor, care was taken not to inject supramaximal doses as these will induce tachyphylaxis. Therefore, as responses became apparent, 0.3 or 0.5 log unit increments were used. A site was used for a dose-response determination only every ½ to 1 hour.

The amplitude of the calibration response to field stimulation in each site was measured and used as 100% for that site. The amplitude of the response to the agonist at each dose was determined, calculated as a % of the calibration response and plotted against the concentration. The $ED_{50}$ of the response represents the amount of agonist required to produce a response which was 50% of the calibration response. It reflects both the efficacy of the response and the potency and does not really distinguish clearly between them.

TABLE 1

Potency of Motilin Receptor Agonists In Binding and In Contractility Experiments

| Compound | $pIC_{50}$ | $pEC_{50}$ |
| --- | --- | --- |
| [Leu$^{13}$]pMOT(1–22) SEQ ID NO:3 | 9.18 | 8.13 |
| [Leu$^{13}$]pMOT(1–14) SEQ ID NO:27 | 8.36 | 7.55 |
| cyclo$^{10,14}$[Glu$^{10}$, Leu$^{13}$, Lys$^{14}$]pMOT(1–14) amide SEQ ID NO:4 | 8.69 | 7.33 |
| cyclo$^{10,14}$[Asp$^{10}$, Leu$^{13}$, Lys$^{14}$]pMOT(1–14) amide SEQ ID NO:6 | 8.82 | 7.77 |
| cyclo$^{10,14}$[Lys$^{10}$, Leu$^{13}$, Asp$^{14}$]pMOT(1–14) amide SEQ ID NO:7 | 8.83 | 7.37 |
| cyclo$^{10,14}$[Glu$^{10}$,Leu$^{13}$,Orn$^{14}$]pMOT(1–14) amide SEQ ID NO:5 | 8.59 | 7.63 |
| cyclo$^{10,14}$[N-MePhe$^{1}$,Asp$^{10}$,Ala$^{11}$,Leu$^{13}$,Lys$^{14}$, Lys$^{15}$]pMOT(1–15) amide SEQ ID NO:8 | 8.96 | 7.69 |
| cyclo$^{10,14}$[N-MePhe$^{1}$,Asp$^{10}$,Ala$^{11}$,Leu$^{13}$,Lys$^{14}$, D-Lys$^{15}$]pMOT(1–15) amide SEQ ID NO:9 | 9.18 | 7.89 |
| cyclo$^{10,14}$[N-MePhe$^{1}$,Glu$^{10}$,Ala$^{11}$,Leu$^{13}$,Lys$^{14}$, Lys$^{15}$]pMOT(1–15) amide SEQ ID NO:10 | 9.20 | 7.96 |
| cyclo$^{10,14}$[Me$_3$N$^+$Phe$^{1}$,Asp$^{10}$,Ala$^{11}$,Leu$^{13}$,Lys$^{14}$, D-Lys$^{15}$]pMOT(1–15) amide SEQ ID NO:11 | 8.91 | 7.89 |
| cyclo$^{10,14}$[N-MePhe$^{1}$,Asp$^{10}$,Ala$^{11}$,D-Arg$^{12}$,Leu$^{13}$, Lys$^{14}$,Lys$^{15}$]pMOT(1–15) amide SEQ ID NO:12 | 8.76 | 7.81 |
| cyclo$^{10,14}$[N-Me-D-Phe$^{1}$,Glu$^{10}$,Leu$^{13}$,Lys$^{14}$] pMOT(1–14) amide SEQ ID NO:13 | 8.26 | 6.87 |
| cyclo$^{10,14}$[Me$_3$N$^+$Phe$^{1}$,Glu$^{10}$,Leu$^{13}$,Lys$^{14}$] pMOT(1–14) amide SEQ ID NO:14 | 8.61 | 7.38 |
| cyclo$^{10,14}$[N-MePhe$^{1}$,Glu$^{10}$,Ala$^{11}$,D-Arg$^{12}$, Leu$^{13}$,Lys$^{14}$,Lys$^{15}$]pMOT(1–15) amide SEQ ID NO:15 | 8.99 | 7.68 |
| cyclo$^{10,14}$[Me$_3$N$^+$Phe$^{1}$,Asp$^{10}$,Ala$^{11}$Leu$^{13}$, Lys$^{14}$]pMOT(1–14) amide SEQ ID NO:16 | 8.65 | 6.98 |
| cyclo$^{10,14}$[N-MePhe$^{1}$,Asp$^{10}$,Ala$^{11}$,Leu$^{13}$,Lys$^{14}$] pMOT(1–14) amide SEQ ID NO:17 | 9.24 | 7.95 |
| cyclo$^{10,14}$[Me$_3$N$^+$Phe$^{1}$,Asp$^{10}$,Ala$^{11}$,Leu$^{13}$,Lys$^{14}$, Lys$^{15}$]pMOT(1–15) amide SEQ ID NO:18 | 8.75 | 7.72 |
| cyclo$^{10,14}$[ME$_3$N$^+$Phe$^{1}$,Asp$^{10}$,Ala$^{11}$,D-Arg$^{12}$,Leu$^{13}$, Lys$^{14}$,Lys$^{15}$]pMOT(1–15) amide SEQ ID NO:19 | 8.54 | 7.72 |
| cyclo$^{10,14}$[Me$_3$N$^+$Phe$^{1}$,Glu$^{10}$,Ala$^{11}$,D-Arg$^{12}$,Leu$^{13}$, Lys$^{14}$,Lys$^{15}$]pMOT(1–15) amide SEQ ID NO:20 | 8.81 | 7.34 |
| cyclo$^{10,14}$[Me$_3$N$^+$Phe$^{1}$,Glu$^{10}$,Ala$^{11}$,Leu$^{13}$, Lys$^{14}$,Lys$^{15}$]pMOT(1–15) amide SEQ ID NO:21 | 8.87 | 7.76 |
| cyclo$^{10,14}$[N-MePhe$^{1}$,Glu$^{10}$,Leu$^{13}$,Lys$^{14}$]pMOT (1–14) amide SEQ ID NO:22 | 9.04 | 8.73 |
| cyclo$^{10,14}$[N-MePhe$^{1}$,Asp$^{10}$,Ala$^{11}$,D-Arg$^{12}$,Leu$^{13}$, Lys$^{14}$]pMOT(1–14) amide SEQ ID NO:23 | 7.94 | 7.89 |
| cyclo$^{10,14}$[Me$_3$N$^+$Phe$^{1}$,Asp$^{10}$,Ala$^{11}$,D-Arg$^{12}$,Leu$^{13}$, Lys$^{14}$]pMOT(1–14) amide SEQ ID NO:24 | 7.90 | 7.02 |

TABLE 2

Half-lives of Motilin Receptor Agonists in 2% Hog Kidney Homogenate

| Compound | $T_{1/2}$ (min) |
| --- | --- |
| [Leu$^{13}$]pMOT(1–22) SEQ ID NO:3 | 30.2 |
| [Leu$^{13}$]pMOT(1–14) SEQ ID NO:27 | 7.5 |
| cyclo$^{10,14}$[N-MePhe$^1$,Glu$^{10}$,Ala$^{11}$,Leu$^{13}$,Lys$^{14}$,Lys$^{15}$]pMOT (1–15) amide SEQ ID NO:10 | 21 |
| cyclo$^{10,14}$[M$_3$N$^+$Phe$^1$,Asp$^{10}$,Ala$^{11}$,Leu$^{13}$,Lys$^{14}$,D-Lys$^{15}$]pMOT (1–15) amide SEQ ID NO:11 | 437 |
| cyclo$^{10,14}$[N-MePhe$^1$,Asp$^{10}$,Ala$^{11}$,D-Arg$^{12}$,Leu$^{13}$,Lys$^{14}$,Lys$^{15}$]pMOT(1–15) amide SEQ ID NO:12 | 16 |
| cyclo$^{10,14}$[Me$_3$N$^+$Phe$^1$,Glu$^{10}$,Leu$^{13}$,Lys$^{14}$]pMOT(1–14) amide SEQ ID NO:14 | >200 |
| cyclo$^{10,14}$[N-Phe$^1$,Glu$^{10}$,Ala$^{11}$,D-Arg$^{12}$,Leu$^{13}$,Lys$^{14}$,Lys$^{15}$]pMOT(1–15) amide SEQ ID NO:15 | 39 |
| cyclo$^{10,14}$[Me$_3$N$^+$Phe$^1$,Asp$^{10}$,Ala$^{11}$,Leu$^{13}$,Lys$^{14}$]pMOT(1–14) amide SEQ ID NO:16 | 103 |
| cyclo$^{10,14}$[N-MePhe$^1$,Asp$^{10}$,Ala$^{11}$,Leu$^{13}$,Lys$^{14}$]pMOT(1–14) amide SEQ ID NO:17 | 31 |
| cyclo$^{10,14}$[Me$_3$N$^+$Phe$^1$,Asp$^{10}$,Ala$^{11}$,Leu$^{13}$,Lys$^{14}$,Lys$^{15}$]pMOT (1–15) amide SEQ ID NO:18 | 413 |
| cyclo$^{10,14}$[Me$_3$N$^+$Phe$^1$,Asp$^{10}$,Ala$^{11}$,D-Arg$^{12}$,Leu$^{13}$,Lys$^{14}$,Lys$^{15}$]pMOT(1–15) amide SEQ ID NO:19 | 85 |
| cyclo$^{10,14}$[Me$_3$N$^+$Phe$^1$,Glu$^{10}$,Ala$^{11}$,D-Arg$^{12}$,Leu$^{13}$, Lys$^{14}$,Lys$^{15}$]pMOT(1–15) amide SEQ ID NO:20 | 49 |
| cyclo$^{10,14}$[Me$_3$N$^+$Phe$^1$,Glu$^{10}$,Ala$^{11}$,Leu$^{13}$,Lys$^{14}$,Lys$^{15}$]pMOT (1–15) amide SEQ ID NO:21 | 267 |
| cyclo$^{10,14}$[N-MePhe$^1$,Glu$^{10}$,Leu$^{13}$,Lys$^{14}$]pMOT(1–14) amide SEQ ID NO:22 | 35 |

Potency of Motilin Receptor Agonists in the Canine Gastrointestinal Tract

| Compound | ED$_{50}$* |
| --- | --- |
| [Leu$^{13}$]pMOT(1–22) SEQ ID NO:3 | 0.04 |
| [Leu$^{13}$]pMOT(1–14) SEQ ID NO:27 | 1.54 |
| cyclo$^{10,14}$[N-MePhe$^1$,Asp$^{10}$,Ala$^{11}$,Leu$^{13}$,Lys$^{14}$,Lys$^{15}$]pMOT (1–15) amide SEQ ID NO:8 | 0.04 |
| cyclo$^{10,14}$[N-MePhe$^1$,Asp$^{10}$,Ala$^{11}$,Leu$^{13}$,Lys$^{14}$,D-Lys$^{15}$] pMOT (1–15) amide SEQ ID NO:9 | 0.04 |
| cyclo$^{10,14}$[N-MePhe$^1$,Glu$^{10}$,Ala$^{11}$,Leu$^{13}$,Lys$^{14}$,Lys$^{15}$]pMOT (1–15) amide SEQ ID NO:10 | 0.002 |
| cyclo$^{10,14}$[Me$_3$N$^+$Phe$^1$,Asp$^{10}$,Ala$^{11}$,Leu$^{13}$,Lys$^{14}$,D-Lys$^{15}$] pMOT (1–15) amide SEQ ID NO:11 | 0.42 |
| cyclo$^{10,14}$[N-MePhe$^1$,Asp$^{10}$,Ala$^{11}$,D-Arg$^{12}$,Leu$^{13}$, SEQ ID NO:12 | 1.00 |
| cyclo$^{10,14}$ [Me$_3$N$^+$Phe$^1$,Glu$^{10}$,Leu$^{13}$,Lys$^{14}$]pMOT(1–14) amide SEQ ID NO:14 | 0.36 |
| cyclo$^{10,14}$[N-MePhe$^1$,Glu$^{10}$,Ala$^{11}$,D-Arg$^{12}$,Leu$^{13}$, Lys$^{14}$,Lys$^{15}$]pMOT(1–15) amide SEQ ID NO:15 | 0.03 |
| cyclo$^{10,14}$[Me$_3$N$^+$Phe$^1$,Asp$^{10}$,Ala$^{11}$Leu$^{13}$,Lys$^{14}$]pMOT(1–14) amide SEQ ID NO:16 | 0.15 |
| cyclo$^{10,14}$[N-MePhe$^1$,Asp$^{10}$,Ala$^{11}$,Leu$^{13}$,Lys$^{14}$]pMOT(1–14) amide SEQ ID NO:17 | 0.01 |
| cyclo$^{10,14}$[Me$_3$N$^+$Phe$^1$,Asp$^{10}$,Ala$^{11}$,Leu$^{13}$,Lys$^{14}$,Lys$^{15}$] pMOT (1–15) amide SEQ ID NO:18 | 0.30 |
| cyclo$^{10,14}$[Me$_3$N$^+$Phe$^1$,Asp$^{10}$,Ala$^{11}$,D-Arg$^{12}$,Leu$^{13}$, Lys$^{14}$,Lys$^{15}$]pMOT(1–15) amide SEQ ID NO:19 | 0.40 |
| cyclo$^{10,14}$[Me$_3$N$^+$Phe$^1$,Glu$^{10}$,Ala$^{11}$,Leu$^{13}$,Lys$^{14}$,Lys$^{15}$] pMOT (1–15) amide SEQ ID NO:21 | 0.34 |
| cyclo$^{10,14}$[N-MePhe$^1$,Glu$^{10}$,Leu$^{13}$,Lys$^{14}$]pMOT(1–14) amide SEQ ID NO:22 | 0.04 |
| cyclo$^{10,14}$[N-MePhe$^1$,Asp$^{10}$,Ala$^{11}$,D-Arg$^{12}$,Leu$^{13}$, Lys$^{14}$]pMOT(1–14) amide SEQ ID NO:23 | 3.00 |

While a number of embodiments of this invention have been represented, it is apparent that the basic construction can be altered to provide other embodiments which utilize the invention without departing from the spirit and scope of the invention. All such modifications and variations are intended to be included within the scope of the invention as defined in the appended claims rather than the specific embodiments which have been presented by way of example.

We claim:

1. A cyclic polypeptide having gastrointestinal motor stimulating activity which may be represented by formula (1):

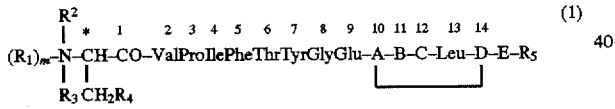

SEQ ID NO:2 including optically active isomeric forms and the pharmaceutically acceptable acid addition salts thereof, wherein groups A and D are linked to from a cyclic structure; and $R_1$ is lower alkyl;

$R_2$ is hydrogen or lower alkyl;

$R_3$ is hydrogen or lower alkyl;

$R_4$ is phenyl or substituted phenyl, wherein the phenyl group may be substituted with one or more substituents selected from the group consisting of halogen, hydroxy, and lower alkoxy;

$R_5$ is —OH or —$NH_2$;

A is selected from the group consisting of L-glutamic acid, L-aspartic acid, L-lysine, L-ornithine, and L-2,4-diaminobutyric acid;

B is L-alanine or L-glutamine;

C is L-arginine or D-arginine;

D is selected from the group consisting of L-lysine, L-ornithine, L-2,4-diaminobutyric acid, L-glutamic acid, and L-aspartic acid;

F is a direct bond between group D and group $R_5$ or is L-lysine or D-lysine;

m is 0 or 1;

the symbol * represents an asymmetric carbon atom which may be in the D or L configuration, with the proviso that:

(a) when A is L-glutamic acid or L-aspartic acid, D is L-lysine, L-ornithine, or L-2,4-diaminobutyric acid; and (b) when A is L-lysine, L-ornithine, or L-2,4-diaminobutyric acid, D is L-glutamic acid or L-aspartic acid.

2. The polypeptide according to claim 1, wherein m is 0.

3. The polypeptide according to claim 1, wherein $R_2$ is selected from the group consisting of methyl, ethyl, propyl, and isopropyl.

4. The polypeptide according to claim 1, wherein $R_3$ is hydrogen.

5. The polypeptide according to claim 1, wherein $R_4$ is phenyl or phenyl substituted with one or more substituents selected from the group consisting of halogen, hydroxy and lower alkoxy.

6. The polypeptide according to claim 1, wherein $(R_1)_m (R_2)(R_3)N$—*$CH(CH_2R_4)CO$— is selected from the group consisting of $CH_3NH$—$CH(CH_2C_6H_5)CO$—,$(CH_3)_2N$—$CH(CH_2C_6H_5)CO$, and $(CH_3)_3N^+$—$CH(CH_2C_6H_5)CO$—.

7. The polypeptide according to claim 1, wherein $R_5$ is —$NH_2$.

8. The polypeptide according to claim 1, wherein A is L-glutamic acid or L-aspartic acid.

9. The polypeptide according to claim 1, wherein B is L-alanine.

10. The polypeptide according to claim 1, wherein C is L-arginine.

11. The polypeptide according to claim 1, wherein D is selected from the group consisting of L-lysine and L-ornithine.

12. The polypeptide according to claim 1, wherein E is L-lysine.

13. The polypeptide according to claim 1, wherein the polypeptide is

SEQ ID NO:10 and its pharmaceutically acceptable addition salts.

14. The polypeptide according to claim 1, wherein the polypeptide is

SEQ ID NO:17 and its pharmaceutically acceptable addition salts.

15. The polypeptide according to claim 1, wherein the polypeptide is

SEQ ID NO:22 and its pharmaceutically acceptable addition salts.

16. The polypeptide according to claim 1, wherein the polypeptide is

SEQ ID NO:11 and its pharmaceutically acceptable addition salts.

17. The polypeptide according to claim 1, wherein the polypeptide is

SEQ ID NO:18 and its pharmaceutically acceptable addition salts.

18. The polypeptide according to claim 1, wherein the polypeptide is

SEQ ID NO:21 and its pharmaceutically acceptable addition salts.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 22 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Phe Val Pro Ile Phe Thr Tyr Gly Glu Leu Gln Arg Met Gln Glu Lys
1               5                   10                  15

Glu Arg Asn Lys Gly Gln
            20

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:2:

Val Pro Ile Phe Thr Tyr Gly Glu
1               5

( 2 ) INFORMATION FOR SEQ ID NO:3:

( i ) SEQUENCE CHARACTERISTICS:
        ( A ) LENGTH: 22 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:3:

Phe Val Pro Ile Phe Thr Tyr Gly Glu Leu Gln Arg Met Gln Glu Lys
1               5                   10                  15

Glu Arg Asn Lys Gly Gln
            20

( 2 ) INFORMATION FOR SEQ ID NO:4:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:4:

Phe Val Pro Ile Phe Thr Tyr Gly Glu Glu Gln Arg Leu Lys
1               5                   10

( 2 ) INFORMATION FOR SEQ ID NO:5:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:5:

Phe Val Pro Ile Phe Thr Tyr Gly Glu Glu Gln Arg Leu Xaa
1               5                   10

( 2 ) INFORMATION FOR SEQ ID NO:6:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:6:

Phe Val Pro Ile Phe Thr Tyr Gly Glu Asp Gln Arg Leu Lys
1               5                   10

( 2 ) INFORMATION FOR SEQ ID NO:7:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:7:

Phe Val Pro Ile Phe Thr Tyr Gly Glu Lys Gln Arg Leu Asp
1               5                   10

( 2 ) INFORMATION FOR SEQ ID NO:8:

( i ) SEQUENCE CHARACTERISTICS:
        ( A ) LENGTH: 15 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:8:

Phe Val Pro Ile Phe Thr Tyr Gly Glu Asp Ala Arg Leu Lys Lys
1               5                   10                  15

( 2 ) INFORMATION FOR SEQ ID NO:9:

( i ) SEQUENCE CHARACTERISTICS:
    ( A ) LENGTH: 15 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:9:

Phe Val Pro Ile Phe Thr Tyr Gly Glu Asp Ala Arg Leu Lys Lys
1               5                   10                  15

( 2 ) INFORMATION FOR SEQ ID NO:10:

( i ) SEQUENCE CHARACTERISTICS:
    ( A ) LENGTH: 15 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:10:

Phe Val Pro Ile Phe Thr Tyr Gly Glu Glu Ala Arg Leu Lys Lys
1               5                   10                  15

( 2 ) INFORMATION FOR SEQ ID NO:11:

( i ) SEQUENCE CHARACTERISTICS:
    ( A ) LENGTH: 15 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:11:

Phe Val Pro Ile Phe Thr Tyr Gly Glu Asp Ala Arg Leu Lys Lys
1               5                   10                  15

( 2 ) INFORMATION FOR SEQ ID NO:12:

( i ) SEQUENCE CHARACTERISTICS:
    ( A ) LENGTH: 15 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:12:

Phe Val Pro Ile Phe Thr Tyr Gly Glu Asp Ala Arg Leu Lys Lys
1               5                   10                  15

( 2 ) INFORMATION FOR SEQ ID NO:13:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:13:

```
Phe Val Pro Ile Phe Thr Tyr Gly Glu Glu Gln Arg Leu Lys
1               5                   10
```

( 2 ) INFORMATION FOR SEQ ID NO:14:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:14:

```
Phe Val Pro Ile Phe Thr Tyr Gly Glu Glu Gln Arg Leu Lys
1               5                   10
```

( 2 ) INFORMATION FOR SEQ ID NO:15:

( i ) SEQUENCE CHARACTERISTICS:
    ( A ) LENGTH: 15 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:15:

```
Phe Val Pro Ile Phe Thr Tyr Gly Glu Glu Ala Arg Leu Lys Lys
1               5                   10                  15
```

( 2 ) INFORMATION FOR SEQ ID NO:16:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:16:

```
Phe Val Pro Ile Phe Thr Tyr Gly Glu Asp Ala Arg Leu Lys
1               5                   10
```

( 2 ) INFORMATION FOR SEQ ID NO:17:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:17:

```
Phe Val Pro Ile Phe Thr Tyr Gly Glu Asp Ala Arg Leu Lys
1               5                   10
```

( 2 ) INFORMATION FOR SEQ ID NO:18:

( i ) SEQUENCE CHARACTERISTICS:
    ( A ) LENGTH: 15 amino acids
    ( B ) TYPE: amino acid
    ( C ) STRANDEDNESS: unknown
    ( D ) TOPOLOGY: unknown ( i i ) MOLECULE TYPE: protein ( i i i ) HYPOTHETICAL: NO ( i v ) ANTI-SENSE: NO ( x i ) SEQUENCE DESCRIPTION: SEQ ID NO:18:

```
Phe Val Pro Ile Phe Thr Tyr Gly Glu Asp Ala Arg Leu Lys Lys
1               5                   10                  15
```

( 2 ) INFORMATION FOR SEQ ID NO:19:

( i ) SEQUENCE CHARACTERISTICS:
    ( A ) LENGTH: 15 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:19:

```
Phe Val Pro Ile Phe Thr Tyr Gly Glu Asp Ala Arg Leu Lys Lys
1               5                   10                  15
```

( 2 ) INFORMATION FOR SEQ ID NO:20:

( i ) SEQUENCE CHARACTERISTICS:
    ( A ) LENGTH: 15 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:20:

```
Phe Val Pro Ile Phe Thr Tyr Gly Glu Glu Ala Arg Leu Lys Lys
1               5                   10                  15
```

( 2 ) INFORMATION FOR SEQ ID NO:21:

( i ) SEQUENCE CHARACTERISTICS:
  ( A ) LENGTH: 15 amino acids
  ( B ) TYPE: amino acid
  ( C ) STRANDEDNESS: unknown
  ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:21:

Phe Val Pro Ile Phe Thr Tyr Gly Glu Glu Ala Arg Leu Lys Lys
1               5                   10                  15

( 2 ) INFORMATION FOR SEQ ID NO:22:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:22:

Phe Val Pro Ile Phe Thr Tyr Gly Glu Glu Gln Arg Leu Lys
1               5                   10

( 2 ) INFORMATION FOR SEQ ID NO:23:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:23:

Phe Val Pro Ile Phe Thr Tyr Gly Glu Asp Ala Arg Leu Lys
1               5                   10

( 2 ) INFORMATION FOR SEQ ID NO:24:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:24:

Phe Val Pro Ile Phe Thr Tyr Gly Glu Asp Ala Arg Leu Lys
1               5                   10

( 2 ) INFORMATION FOR SEQ ID NO:25:

( i ) SEQUENCE CHARACTERISTICS:
   ( A ) LENGTH: 15 amino acids
   ( B ) TYPE: amino acid
   ( C ) STRANDEDNESS: unknown
   ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:25:

```
Phe Val Pro Ile Phe Thr Tyr Gly Glu Glu Ala Arg Leu Lys Lys
1               5                   10                  15
```

( 2 ) INFORMATION FOR SEQ ID NO:26:

( i ) SEQUENCE CHARACTERISTICS:
   ( A ) LENGTH: 15 amino acids
   ( B ) TYPE: amino acid
   ( C ) STRANDEDNESS: unknown
   ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:26:

```
Phe Val Pro Ile Phe Thr Tyr Gly Glu Glu Ala Arg Leu Lys Lys
1               5                   10                  15
```